(12) United States Patent
Carroll et al.

(10) Patent No.: US 6,518,279 B2
(45) Date of Patent: *Feb. 11, 2003

(54) CYCLOPENTANONE DIHYDROPYRIDINE COMPOUNDS USEFUL AS POTASSIUM CHANNEL OPENERS

(75) Inventors: William A. Carroll, Evanston, IL (US); Yiyuan Chen, Waukegan, IL (US); Irene Drizin, Wadsworth, IL (US); James F. Kerwin, Grayslake, IL (US); Jimmie L. Moore, Gurnee, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/262,441

(22) Filed: Mar. 4, 1999

(65) Prior Publication Data

US 2002/0007065 A1 Jan. 17, 2002

(51) Int. Cl.$^7$ ................. A61K 31/4353; C07D 221/06
(52) U.S. Cl. .......................................... 514/290; 546/79
(58) Field of Search ............................ 546/79; 514/290

(56) References Cited

U.S. PATENT DOCUMENTS

| 4,895,855 A | 1/1990 | Goldmann et al. |
| 5,248,681 A | 9/1993 | Cooper |

FOREIGN PATENT DOCUMENTS

| DE | 2003148 | 7/1971 |
| EP | 0186027 | 7/1986 |
| EP | 0299727 | 11/1991 |
| EP | 0539153 | 4/1993 |
| EP | 0539154 | 4/1993 |
| EP | 0622366 | 11/1994 |
| WO | 9408966 | 4/1994 |
| WO | 9931059 | 6/1999 |

OTHER PUBLICATIONS

Frank, C.A., et al., "Dihydropyridine Katp Potassium Channel Openers", *Bioorganic and Medicinal Chemistry*, 3:2725–2726–67 (1993).

Dimmock, J. R., et al., "Evaluation of Mannich bases of 2-arylidene-1,3-diketones versus murine P388 leukemia", *Eur. J. Med. Chem.*, 23:111–117 (1988).

*Primary Examiner*—Patricia L. Morris
(74) *Attorney, Agent, or Firm*—Portia Chen; Michael J. Ward

(57) ABSTRACT

Compounds of formula I

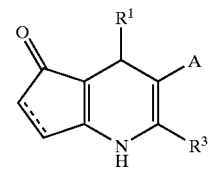

are useful in treating diseases prevented by or ameliorated with potassium channel openers. Also disclosed are potassium channel opening compositions and a method of opening potassium channels in a mammal.

10 Claims, No Drawings

CYCLOPENTANONE DIHYDROPYRIDINE COMPOUNDS USEFUL AS POTASSIUM CHANNEL OPENERS

TECHNICAL FIELD

Novel, water soluble dihydropyridine compounds and their derivatives can open potassium channels and are useful for treating a variety of medical conditions.

BACKGROUND OF INVENTION

Potassium channels play an important role in regulating cell membrane excitability. When the potassium channels open, changes in the electrical potential across the cell membrane occur and result in a more polarized state. A number of diseases or conditions can be treated with therapeutic agents that open potassium channels. See K. Lawson, *Pharmacol. Ther.*, v. 70, pp. 39–63 (1996); D. R. Gehlert et al., *Prog. NeuroPsychopharmacol & Biol. Psychiat.*, v. 18, pp. 1093–1102 (1994); M. Gopalakrishnan et al., *Drug Development Research*, v. 28, pp. 95–127 (1993); J. E. Freedman et al., *The Neuroscientist*, v. 2, pp. 145–152 (1996). Such diseases or conditions include asthma, epilepsy, hypertension, impotence, migraine, pain, urinary incontinence, stroke, Raynaud's Syndrome, eating disorders, functional bowel disorders, and neurodegeneration.

Potassium channel openers also act as smooth muscle relaxants. Because urinary incontinence can result from the spontaneous, uncontrolled contractions of the smooth muscle of the bladder, the ability of potassium channel openers to hyperpolarize bladder cells and relax bladder smooth muscle provides a method to ameliorate or prevent urinary incontinence.

DE 2003148 discloses acridinedione and quinolone compounds claimed to possess spasmolytic action on the smooth muscle of the gastrointestinal tract, the urogenital tract and the respiratory system. Compunds disclosed in DE 2003148 are also claimed to have antihypertensive properties. These compounds belong to the larger general chemical class of dihydropyridines. The examples described in DE 2003148 all possess a cyclohexanone ring fused to the dihydropyridine nucleus and as a result have the disadvantage of possessing very low water solubility. This low solubility limits the utility of these agents as pharmaceuticals. Low water solubility can result in erratic patterns of absorption when drugs are administered orally. This can result in wide variability in drug absorption from patient to patient and potentially to toxic side-effects. The compounds of the present invention are chemically distinct from the examples described in DE 2003148 since they must have a cyclopentanone ring fused to the dihydropyridine ring, a structural feature that confers upon the compounds of the present invention the surprising and unexpected property of vastly superior water solubility, on average 55 times higher solubility in water than comparable analogs from DE 2003148.

WO 9408966, EP 0539153 A1 and EP 0539154 A1 disclose acridinedione and quinolone compounds that are claimed useful in the treatment of urinary incontinence. These compounds belong to the larger general chemical class of dihydropyridines. The examples described in WO 9408966, EP 0539153 A1 and EP 0539154 A1 all possess a cyclohexanone ring fused to the dihydropyridine nucleus and as a result have the disadvantage of possessing very low water solubility. This low solubility limits the utility of these agents as pharmaceuticals. Low water solubility can result in erratic patterns of absorption when drugs are administered orally. This can result in wide variability in drug absorption from patient to patient and potentially to toxic side-effects. The compounds of the present invention are chemically distinct from those of WO94/08966, EP 0539153 A1 and EP 0539154 A1 since they must have a cyclopentanone ring fused to the dihydropyridine ring, a structural feature that confers upon the compounds of the present invention the surprising and unexpected property of vastly superior water solubility, on average 55 times higher solubility in water than comparable analogs from the above inventions.

Dihydropyridines of differing chemical structure may possess a variety of biological activities. Dimmock et al (*Eur. J. Med. Chem.* 1988, 23, 111–117) describe a N-methyldihydropyridine containing two cyclopentanone rings fused to the dihydropyridine nucleus. The only biological activity indicated was that it was inactive against murine P388 lymphocytic leukemia. The compounds of the present invention are distinct from this compound since they must be unsubstituted at the dihydropyridine nitrogen.

EP 622366 A1 describes dihydropyridines substituted with quinolines as cardiovascular agents.

EP 299727 describes 4-aryl-(5,6-bicyclo)-2-(imidazol-1-ylalkoxymethyl)dihydropyridines as platelet activating factor (PAF) antagonists.

WO 9012015-A describes dihydropyridines that are claimed to be PAF antagonists. EP 173943-A describes dihydropyridines that are modifiers of enzymes involved in arachidonic acid metabolism. EP 186027-A describes dihydropyridines that have vasodilating properties. All of these patents describe dihydropyridines that generically claim a cyclopentanone fused on one side of the dihydropyridine with carboxylic esters on the other side.

Thus, the compounds of the present invention are chemically distinct from the prior art, are water soluble, hyperpolarize cell membranes, open potassium channels, relax smooth muscle cells, inhibit bladder contractions and are useful for treating diseases that can be ameliorated by opening potassium channels.

SUMMARY OF THE INVENTION

In its principle embodiment, the present invention discloses compounds having formula I:

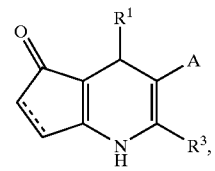

or a pharmaceutically acceptable salt, ester, amide, or prodrug thereof wherein, a broken line represents the presence of an optional double bond;

$R^1$ is selected from the group consisting of aryl and heteroaryl;

A is selected from the group consisting of hydrogen, alkyl, cyano, haloalkyl, heteroaryl, nitro, and —C(O)$R^2$, wherein, $R^2$ is selected from the group consisting of alkyl, haloalkyl, and hydroxy;

$R^3$ is selected from the group consisting of hydrogen, alkyl, and haloalkyl; and A and $R^3$ taken together with the ring to which they are attached can form a 5- or 6-membered carbocyclic ring, said 5- or 6-membered carbocyclic ring can contain 1 or 2 double bonds, and can be substituted with 1 or 2 substituents selected from the group consisting of alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

Another embodiment of the present invention relates to pharmaceutical compositions comprising a therapeutically effective amount of a compound of formula I or a pharmaceutically acceptable salt, ester, amide, or prodrug thereof in combination with a pharmaceutically acceptable carrier.

Yet another embodiment of the invention relates to a method of treating asthma, epilepsy, hypertension, Raynaud's syndrome, impotence, migraine, pain, eating disorders, urinary incontinence, functional bowel disorders, neurodegeneration and stroke comprising administering a therapeutically effective amount of a compound of formula I or a pharmaceutically acceptable salt, ester, amide, or prodrug thereof.

DETAILED DESCRIPTION OF THE INVENTION

In one embodiment, compounds of the present invention have formula I:

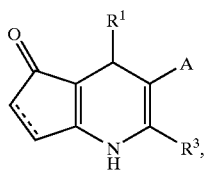

I or a pharmaceutically acceptable salt, ester, amide, or prodrug thereof wherein, a broken line represents the presence of an optional double bond;

R$^1$ is selected from the group consisting of aryl and heteroaryl;

A is selected from the group consisting of hydrogen, alkyl, cyano, haloalkyl, heteroaryl, nitro, and —C(O)R$^2$, wherein, R$^2$ is selected from the group consisting of alkyl, haloalkyl, and hydroxy;

R$^3$ is selected from the group consisting of hydrogen, alkyl, and haloalkyl; and A and R$^3$ taken together with the ring to which they are attached can form a 5- or 6-membered carbocyclic ring, said 5- or 6-membered carbocyclic ring can contain 1 or 2 double bonds, and can be substituted with 1 or 2 substituents selected from the group consisting of alkenyl, alkoxy, alkoxyalkoxy, alkoxyalkyl, alkyl, alkynyl, arylalkoxy, haloalkenyl, haloalkyl, halogen, hydroxy, hydroxyalkyl, hydroxyalkenyl, oxo, and —NR$^4$R$^5$ wherein, R$^4$ and R$^5$ are independently selected from the group consisting of hydrogen and lower alkyl.

In another embodiment of the present invention, compounds have formula I wherein, A is selected from the group consisting of hydrogen, alkyl, cyano, nitro, and haloalkyl; and R$^3$ is hydrogen.

In another embodiment of the present invention, compounds have formula I wherein, A is selected from the group consisting of hydrogen, alkyl, cyano, nitro, and haloalkyl; and R$^3$ is selected from the group consisting of alkyl.

In another embodiment of the present invention, compounds have formula I wherein, A is selected from the group consisting of hydrogen, alkyl, cyano, nitro, and haloalkyl; and R$^3$ is selected from the group consisting of haloalkyl.

In another embodiment of the present invention, compounds have formula I wherein, A is —C(O)R$^2$ wherein R$^2$ is selected from the group consisting of alkyl, haloalkyl, and hydroxy; and R$^3$ is hydrogen.

In another embodiment of the present invention, compounds have formula I wherein, A is —C(O)R$^2$ wherein R$^2$ is selected from the group consisting of alkyl, haloalkyl, and hydroxy; and R$^3$ is selected from the group consisting of alkyl.

In another embodiment of the present invention, compounds have formula I wherein, A is —C(O)R$^2$ wherein R$^2$ is selected from the group consisting of alkyl, haloalkyl, and hydroxy; and R$^3$ is selected from the group consisting of haloalkyl.

In another embodiment of the present invention, compounds have formula I wherein, A is —C(O)R$^2$ wherein R$^2$ is hydroxy; and R$^3$ is selected from the group consisting of alkyl wherein lower alkyl is preferred.

In another embodiment of the present invention, compounds have formula I wherein, A is heteroaryl; and R$^3$ is selected from the group consisting of hydrogen, alkyl, and haloalkyl.

In another embodiment of the present invention, compounds have formula I wherein, A is tetrazole; and R$^3$ is selected from the group consisting of hydrogen, alkyl, and haloalkyl.

In a preferred embodiment, compounds of the present invention have formula II:

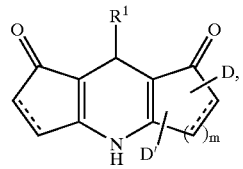

II or a pharmaceutically acceptable salt, ester, amide, or prodrug thereof, wherein, a broken line represents the presence of an optional double bond; m is an integer 1–2; R$^1$ is selected from the group consisting of aryl and heteroaryl; D and D' are independently selected from the group consisting of hydrogen, alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

In another preferred embodiment, compounds of the present invention have formula III:

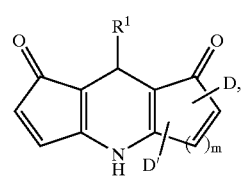

III or a pharmaceutically acceptable salt, ester, amide, or prodrug thereof, wherein, m is an integer 1–2; R$^1$ is selected from the group consisting of aryl and heteroaryl; D and D' are independently selected from the group consisting of hydrogen, alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

In another preferred another embodiment, compounds of the present invention have formula IV:

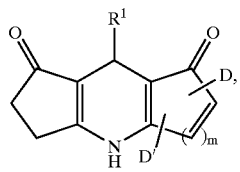

IV or a pharmaceutically acceptable salt, ester, amide, or prodrug thereof, wherein, m is an integer 1–2; R$^1$ is selected from the group consisting of aryl and heteroaryl; D and D' are independently selected from the group consisting of hydrogen, alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

In another preferred embodiment, compounds of the present invention have formula V:

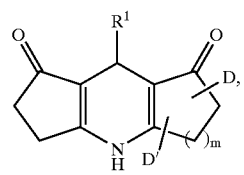

V or a pharmaceutically acceptable salt, ester, amide, or prodrug thereof, wherein m is an integer 1–2; R$^1$ is selected from the group consisting of aryl and heteroaryl; D and D' are independently selected from the group consisting of hydrogen, alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

In a more preferred embodiment of the present invention, compounds have formula V, wherein, m is 1; D is hydrogen; D' is hydrogen; and R$^1$ is aryl wherein, a preferred aryl is phenyl substituted with 1, 2, 3, 4, or 5 substituents independently selected from alkenyl, alkoxy, alkoxycarbonyl, alkyl, alkylcarbonyl, alkylcarbonyloxy, alkylsulfinyl, alkylsulfonyl, alkylthio, alkynyl, aryl, azido, arylalkyl, aryloxy, carboxy, cyano, formyl, halogen, haloalkyl, haloalkyloxy, heteroaryl, hydroxy, methylenedioxy, mercapto, nitro, sulfamyl, sulfo, sulfonate, thioureylene, ureylene, and —C(O)NR$^{80}$R$^{81}$ wherein, R$^{80}$ and R$^{81}$ are independently selected from hydrogen, alkyl, aryl and arylalkyl. Most preferred phenyl substituents are selected from cyano, halogen and nitro.

In another more preferred embodiment of the present invention, compounds have formula V wherein, m is 1; D is hydrogen; D' is hydrogen; and R$^1$ is heteroaryl, more preferred heteroaryls include, but are not limited to, benzoxadiazole, benzoxazole, benzothiazole, benzothiadiazole, benzothiophene, benzofuran, furan, and thiophene. A most preferred heteroaryl is 2,1,3-benzoxadiazole.

In another preferred embodiment, compounds of the present invention have formula VI:

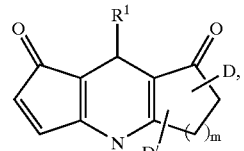

VI or a pharmaceutically acceptable salt, ester, amide, or prodrug thereof, wherein, m is an integer 1–2; R$^1$ is selected from the group consisting of aryl and heteroaryl; D and D' are independently selected from the group consisting of hydrogen, alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein, R$^4$ and R$^5$ are independently selected from the group consisting of hydrogen and lower alkyl.

In another more preferred embodiment of the present invention, compounds have formula VI wherein, m is 2; D is hydrogen; D' is hydrogen; and R$^1$ is aryl wherein, a preferred aryl is phenyl substituted with 1, 2, 3, 4, or 5 substituents independently selected from alkenyl, alkoxy, alkoxycarbonyl, alkyl, alkylcarbonyl, alkylcarbonyloxy, alkylsulfinyl, alkylsulfonyl, alkylthio, alkynyl, aryl, azido, arylalkyl, aryloxy, carboxy, cyano, formyl, halogen, haloalkyl, haloalkyloxy, heteroaryl, hydroxy, methylenedioxy, mercapto, nitro, sulfamyl, sulfo, sulfonate, thioureylene, ureylene, and —C(O)NR$^{80}$R$^{81}$ wherein, R$^{80}$ and R$^{81}$ are independently selected from hydrogen, alkyl, aryl and arylalkyl. Most preferred phenyl substituents are selected from cyano, halogen and nitro.

The present invention also relates to pharmaceutical compositions which comprise a therapeutically effective amount of a compound of formulae I–VI or a pharmaceutically acceptable salt, ester, amide, or prodrug thereof in combination with a pharmaceutically acceptable carrier.

The present invention also relates to a method of treating a disease in a mammal comprising administering an effective amount of a compound of formulae I–VI or a pharmaceutically acceptable salt, ester, amide, or prodrug thereof.

In particular, the present invention relates to a method of treating asthma, epilepsy, hypertension, Raynaud's syndrome, impotence, migraine, pain, eating disorders, urinary incontinence, functional bowel disorders, neurodegeneration and stroke comprising administering an effective amount of a compound of formulae I–VI or a pharmaceutically acceptable salt, ester, amide, or prodrug thereof.

Definition of Terms

As used throughout this specification and the appended claims, the following terms have the following meanings.

The term "alkenyl," as used herein, refers to a straight or branched chain hydrocarbon containing from 2-to-10 carbons and containing at least one carbon—carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkyl," as used herein, refers to a straight or branched chain hydrocarbon containing from 1-to-10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonyloxy," as used herein, refers to an alkylcarbonyl group, as defined herein, appended to the parent molecular moiety through an oxy group, as defined herein. Representative examples of alkylcarbonyloxy include, but are not limited to, acetyloxy, ethylcarbonyloxy, tert-butylcarbonyloxy, and the like.

The term "alkylsulfinyl," as used herein, refers to an alkyl group, as defined herein, appended to the parent molecular moiety through a sulfinyl group, as defined herein. Representative examples of alkylsulfinyl include, but are not limited, methylsulfinyl, ethylsulfinyl, and the like.

The term "alkylsulfonyl," as used herein, refers to an alkyl group, as defined herein, appended to the parent molecular moiety through a sulfonyl group, as defined herein. Representative examples of alkylsulfonyl include, but are not limited, methylsulfonyl, ethylsulfonyl, and the like.

The term "alkylthio," as used herein, refers to an alkyl group, as defined herein, appended to the parent molecular moiety through a thio group, as defined herein. Representative examples of alkylthio include, but are not limited, methylthio, ethylthio, tert-butylthio, hexylthio, and the like.

The term "alkynyl," as used herein, refers to a straight or branched chain hydrocarbon group containing from 2-to-10 carbon atoms and containing at least one carbon—carbon triple bond. Representative examples of alkynyl include, but are not limited, to acetylenyl, 1-propynyl, 2-propynyl, 3-butynyl, 2-pentynyl, 1-butynyl and the like.

The term "amino," as used herein, refers to —NH$_2$.

The term "aminocarbonyl," as used herein, refers to a —C(O)NH$_2$ group.

The term "alkylamino," as used herein, refers to an alkyl group, as defined herein, appended to the parent molecular moiety through an amino group, as defined herein. Representative examples of alkylamino include, but are not limited to, methylamino, ethylamino, propylamino, tert-butylamino, and the like.

The term "dialkylamino," as used herein, refers to two independent alkyl groups, as defined herein, appended to the parent molecular moiety through an amino group, as defined herein. Representative examples of dialkylamino include, but are not limited to, dimethylamino, diethylamino, ethylmethylamino, butylmethylamino, ethylhexylamino, and the like.

The term "aryl," as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The aryl groups of this invention can be substituted with 1, 2, 3, 4, or 5 substituents independently selected from alkenyl, alkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkyl, aryloxy, carboxy, cyano, formyl, halogen, haloalkyl, haloalkoxy, heteroaryl, hydroxy, methylenedioxy, mercapto, nitro, sulfamyl, sulfo, sulfonate, thioureylene, ureylene, —NR$^{80}$R$^{81}$ (wherein, R$^{80}$ and R$^{81}$ are independently selected from hydrogen, alkyl, alkylcarbonyl, aryl, arylalkyl and formyl), and —C(O)NR$^{82}$R$^{83}$ (wherein, R$^{82}$ and R$^{83}$ are independently selected from hydrogen, alkyl, aryl, and arylalkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxy include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "aryloxy," as used herein, refers to an aryl group, as defined herein, appended to the parent molecular moiety through an oxy group, as defined herein.

The term "azido," as used herein, refers to an —N$_3$ group.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, 2-carboxyethyl, 3-carboxypropyl, and the like.

The term "carboxy protecting group," as used herein, refers to a carboxylic acid protecting ester group employed to block or protect the carboxylic acid functionality while the reactions involving other functional sites of the compound are carried out. Carboxy-protecting groups are disclosed in T. H. Greene and P. G. M. Wuts, *Protective Groups in Organic Synthesis,* 2nd edition, John Wiley & Sons, New York (1991), which is hereby incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy-protecting groups are loweralkyl (e.g., methyl, ethyl or tertiary butyl and the like); benzyl (phenylmethyl) and substituted benzyl derivatives thereof such substituents are selected from alkoxy, alkyl, halogen, and nitro groups and the like.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, and the like.

The term "cycloalkyl", as used herein, refers to a saturated cyclic hydrocarbon group containing from 3 to 8 carbon atoms. Representative examples of cycloalkyl include, but are not limited to, cyclopropyl, cyclobutyl, cyclopentyl, cyclohexyl, cycloheptyl, cyclooctyl and the like.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl, and the like.

The term "ethylenedioxy," as used herein, refers to a —O(CH$_2$)$_2$O— group wherein, the oxygen atoms of the ethylenedioxy group are attached to the same carbon atom or the oxygen atoms of the ethylenedioxy group are attached to two adjacent carbon atoms.

The term "formyl,"as used herein, refers to a —C(O)H group.

The term "halo" or "halogen," as used herein, refers to —Cl, —Br, —I or —F.

The term "haloalkenyl," as used herein, refers to at least one halogen, as defined herein, appended to the parent molecular moiety through an alkenyl group, as defined herein. Representative examples of haloalkenyl include, but are not limited to, 4-chlorobuten-1-yl, 4,4,4-trifluorobuten-1-yl, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "haloalkoxy," as used herein, refers to at least one halogen, as defined herein, appended to the parent molecular moiety through an alkoxy group, as defined herein. Representative examples of haloalkoxy include, but are not limited to, 2-chloroethoxy, 2,2,2-trifluoroethoxy, trifluoromethyl, and the like.

The term "heteroaryl," as used herein, refers to a monocyclic- or a bicyclic-ring system. Monocyclic ring systems are exemplified by any 5- or 6-membered ring containing 1, 2, 3, or 4 heteroatoms independently selected from oxygen, nitrogen and sulfur. The 5-membered ring has from 0–2 double bonds and the 6-membered ring has from 0–3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, and thiopyranopyridine.

The heteroaryl groups of this invention can be substituted with 1, 2, or 3 substituents independently selected from alkenyl, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, azido, arylalkoxy, arylalkoxycarbonyl, arylalkyl, aryloxy, carboxy, cyano, cycloalkyl, ethylenedioxy, formyl, halogen, haloalkyl, haloalkoxy, heteroaryl, hydroxy, methylenedioxy, mercapto, nitro, oxo, sulfamyl, sulfo, sulfonate, thioureylene, ureylene, —NR$^{80}$R$^{81}$ (wherein, R$^{80}$ and R$^{81}$ are independently selected from hydrogen, alkyl, alkylcarbonyl, aryl, arylalkyl and formyl), and —C(O)NR$^{82}$R$^{83}$ (wherein, R$^{82}$ and R$^{83}$ are independently selected from hydrogen, alkyl, aryl, and arylalkyl.

The term "hydroxy," as used herein, refers to an —OH group.

The term "hydroxyalkenyl," as used herein, refers to a hydroxy group, as defined herein, appended to the parent molecular moiety through an alkenyl group, as defined herein. Representative examples of hydroxyalkenyl include, but are not limited to, 4-hydroxybuten-1-yl, 5-hydroxypenten-1-yl, and the like.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, and the like.

The term "lower alkoxy," as used herein, refers to a lower alkyl group, as defined herein, appended to the parent molecular moiety through an oxy group, as defined herein. Representative examples of lower alkoxy include, but are not limited to, methoxy, ethoxy, propoxy, 2-propoxy, butoxy, tert-butoxy, and the like.

The term "lower alkyl," as used herein, refers to a straight or branched chain hydrocarbon group containing from 1-to-4 carbon atoms. Representative examples of lower alkyl include, but are not limited to, methyl, ethyl, n-propyl, iso-propyl, n-butyl, iso-butyl, tert-butyl, and the like.

The term "mammal," as used herein, has its ordinary meaning and includes human beings.

The term "mercapto," as used herein, refers to a —SH group.

The term "methylenedioxy," as used herein, refers to a —OCH$_2$O— group wherein, the oxygen atoms of the methylenedioxy group are attached to two adjacent carbon atoms.

The term "nitro," as used herein, refers to a —NO$_2$ group.

The term "oxo," as used herein, refers to a =O moiety.

The term "oxy," as used herein, refers to a —O— moiety.

The term "sulfamyl," as used herein, refers to a —SO$_2$NR$^{94}$R$^{95}$ group, wherein, R$^{94}$ and R$^{95}$ are independently selected from hydrogen, alkyl, aryl, and arylalkyl, as defined herein.

The term "sulfinyl," as used herein, refers to a —S(O)— group.

The term "sulfo," as used herein, refers to a —SO$_3$H group.

The term "sulfonate," as used herein, refers to a —S(O)$_2$OR$^{96}$ group, wherein, R$^{96}$ is selected from alkyl, aryl, and arylalkyl, as defined herein.

The term "sulfonyl," as used herein, refers to a —SO$_2$— group.

The term "thio," as used herein, refers to a —S— moiety.

The term "thioureylene," as used herein, refers to —NR$^{97}$C(S)NR$^{98}$R$^{99}$, wherein, R$^{97}$, R$^{98}$, and R$^{99}$ are independently selected from hydrogen, alkyl, aryl, and arylalkyl, as defined herein.

The term "ureylene," as used herein, refers to —NR$^{97}$C(O)NR$^{98}$R$^{99}$, wherein, R$^{97}$, R$^{98}$, and R$^{99}$ are independently selected from hydrogen, alkyl, aryl, arylalkyl, as defined herein.

Preferred compounds of formula I include, 8-(3-Bromo-4-fluorophenyl)-2,3,4,5,6,8-hexahydrocyclopenta[b,e]pyridine-1,7-dione, 8-(3-Cyanophenyl)-2,3,4,5,6,8-hexahydrocyclopenta[b,e]pyridine-1,7-dione, 8-(4-Chloro-3-nitrophenyl)-2,3,4,5,6,8-hexahydrocyclopenta[b,e]pyridine-1,7-dione, 8-(3-Nitrophenyl)-2,3,4,5,6,8-hexahydrocyclopenta[b,e]pyridine-1,7-dione, 8-(3-Chloro-4-fluorophenyl)-2,3,4,5,6,8-hexahydrocyclopenta[b,e]pyridine-1,7-dione, 8-(3,4-Dichlorophenyl)-2,3,4,5,6,8-hexahydrocyclopenta[b,e]pyridine-1,7-dione, 8-(2,1,3-benzoxadiazol-5-yl)-2,3,4,5,6,8-hexahydrocyclopenta[b,e]pyridine-1,7-dione, and 8-(3-Iodo-4-fluorophenyl)-2,3,4,5,6,8-hexahydrocyclopenta[b,e]pyridine-1,7-dione, and 9-(3-bromo-4-fluorophenyl)-5,6,7,9-tetrahydro-1H-cyclopenta[b]quinoline-1,8(4H)-dione, 4-(3-bromo-4-fluorophenyl)-2-methyl-5-oxo-4,5,6,7-tetrahydro-1H-cyclopenta[b]pyridine-3-carboxylic acid, and pharmaceutically acceptable salts, esters, amides, or prodrugs thereof.

PREPARATION OF COMPOUNDS OF THE INVENTION

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–9. For Schemes 1–9, R$^1$ is selected from aryl and heteroaryl; A is selected from hydrogen, alkyl, cyano, haloalkyl, heteroaryl, nitro, and —C(O)R$^2$ wherein R$^2$ is selected from alkyl, haloalkyl, and hydroxy; R$^3$ is selected from hydrogen, alkyl, and haloalkyl; A and R$^3$ taken together with the carbon atoms to which they are attached can form a 5 or 6 membered carbocyclic ring which can contain 1 or 2 double bonds, and can be substituted with 1 or 2 substituents selected from alkenyl, alkoxy, alkoxyalkoxy, alkoxyalkyl, alkyl, alkynyl, arylalkoxy, haloalkenyl, haloalkyl, halogen, hydroxy, hydroxyalkenyl, hydroxyalkyl, oxo, and —NR$^4$R$^5$ wherein R$^4$ and R$^5$ are independently selected hydrogen and lower alkyl; and a broken line can represent an optional double bond.

Scheme 1

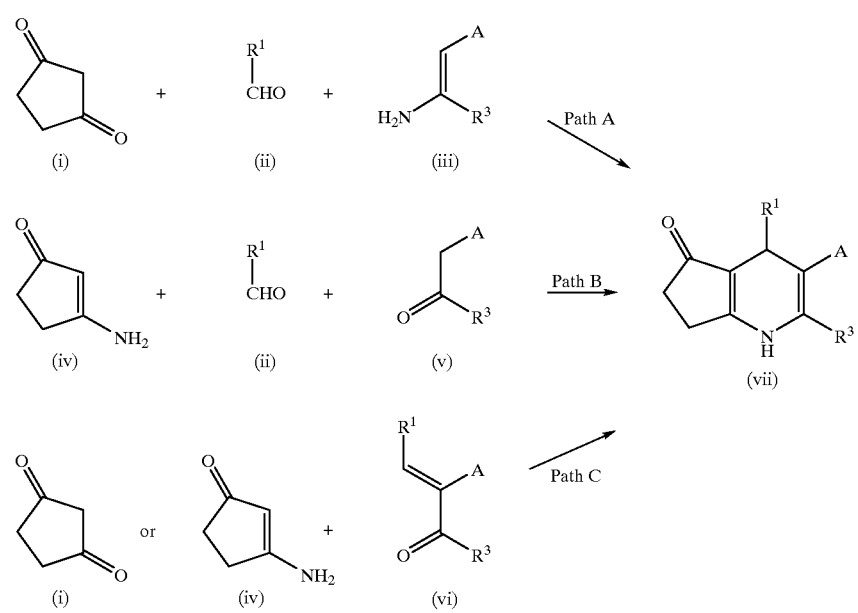

As shown in Scheme 1, the dihydropyridines of formula (vii), wherein $R^1$, $R^3$, and A, are as defined in formula I, can be prepared by one of three general methods. According to Path A, 1,3-cyclopentanedione (i) may be reacted with an aldehyde (ii) and an appropriate enamine component (iii) with heating in a protic solvent such as ethanol, methanol, isopropanol etc. or in dimethylformamide (DMF), or acetonitrile. A subsequent period of heating may be required with an acid such as hydrochloric acid, sulfuric acid or toluenesulfonic acid in order to drive the reaction to completion. According to Path B, 3-amino-2-cyclopenten-1-one (iv) may be reacted with an aldehyde (ii) and an appropriate carbonyl component (v) using the same reaction conditions as for Path A. According to Path C, 1,3-cyclopentanedione (i) together with an ammonia source such as ammonia in ethanol, ammonium acetate, or ammonium hydroxide, may be reacted using the same conditions as for Path A with an enone (vi) component that has been prepared from an aldehyde (ii) and a carbonyl component (v). Alternatively in Path C, 3-amino-2-cyclopenten-1-one (iv) may be substituted for the 1,3-cyclopentanedione (i) and the ammonia source using the same reaction conditions described for Path A.

Scheme 2

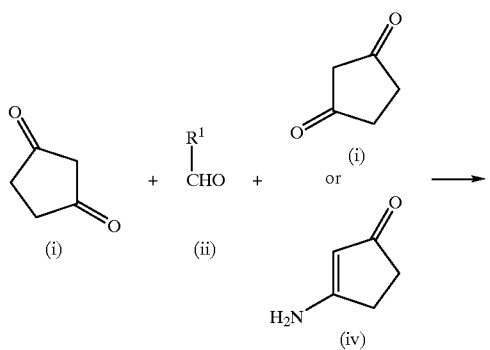

As shown in Scheme 2, dihydropyridines of formula (viii), wherein $R^1$ is defined as in formula I, may be prepared by reacting 2 equivalents of 1,3-cyclopentanedione (i) with an aldehyde (ii) and an ammonia source such as ammonia in ethanol, ammonium acetate or ammonium hydroxide with heating in a protic solvent such as ethanol, methanol, isopropanol etc. or in dimethylformamide (DMF), or acetonitrile. A subsequent period of heating may be required with an acid such as hydrochloric acid, sulfuric acid or toluenesulfonic acid in order to drive the reaction to completion. Alternatively, 1,3-cyclopentanedione (i) may be reacted with an aldehyde (ii) and 3-amino-2-cyclopenten-1-one (iv) heating in the same solvents as above. A subsequent period of heating may be required with an acid such as hydrochloric acid or toluenesulfonic acid in order to drive the reaction to completion.

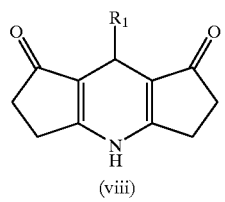

(viii)

Scheme 3

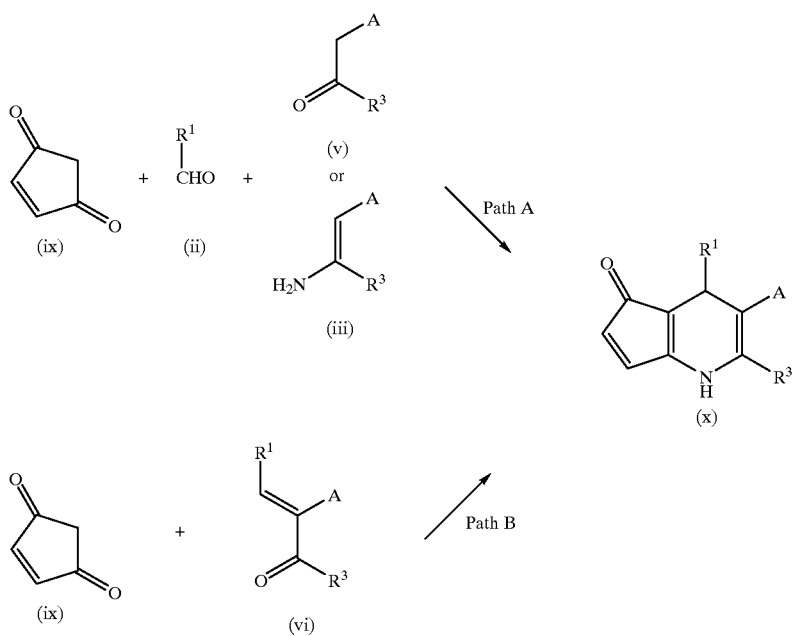

As shown in Scheme 3, the dihydropyridines of formula (x), wherein $R^1$, $R^3$, and A, are as defined in formula I, can be prepared by one of two general methods. According to Path A, 1,3-cyclopentenedione (ix) may be reacted with an aldehyde (ii) and an appropriate carbonyl component (v) together with an ammonia source such as ammonia in ethanol, ammonium acetate, or ammonium hydroxide, with heating in a protic solvent such as ethanol, methanol, isopropanol etc. or in dimethylformamide (DMF), or acetonitrile. A subsequent period of heating may be required with an acid such as hydrochloric acid, sulfuric acid or toluenesulfonic acid in order to drive the reaction to completion. Alternatively, an appropriate enamine (iii) may be substituted for the carbonyl component (v) and ammonia source using the same reaction conditions. According to Path B, 1,3-cyclopentenedione (ix) together with an ammonia source such as ammonia in ethanol, ammonium acetate, or ammonium hydroxide, may be reacted using the same conditions as for Path A with an enone (vi) component that has been prepared from an aldehyde (ii) and a carbonyl component(v).

Scheme 4

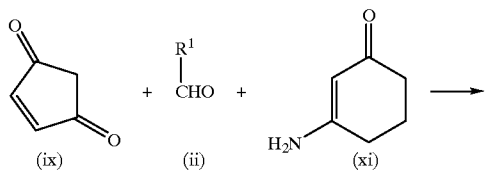

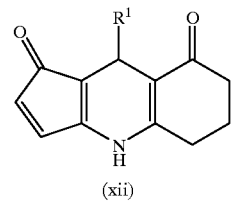

(xii)

As shown in Scheme 4, dihydropyridines of general formula (xii), wherein $R^1$ is defined in formula I, may be prepared by reacting 1,3-cyclopentenedione (ix) with an aldehyde (ii) and 3-amino-2-cyclohexen-1-one (xi) with heating in a protic solvent such as ethanol, methanol, isopropanol etc. or in dimethylformamide (DMF), or acetonitrile.

Scheme 5

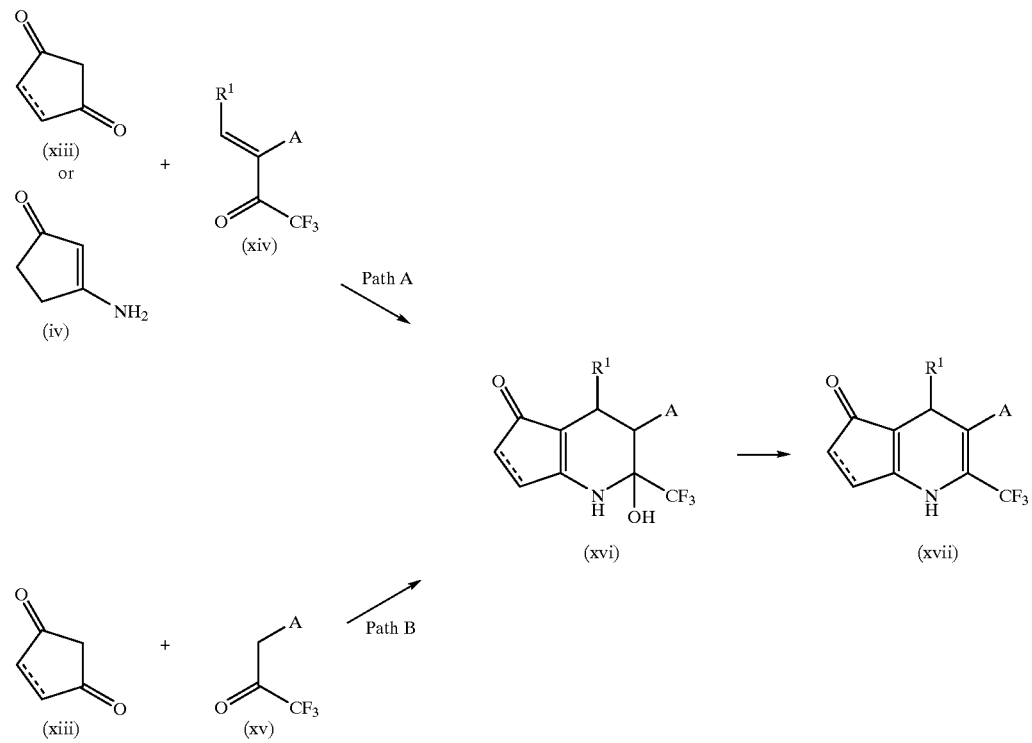

As shown in Scheme 5, the dihydropyridines of formula (xvii), wherein $R^1$ and A are as defined in formula I, can be prepared by one of two general methods. According to Path A, 1,3-cyclopentanedione or 1,3-cyclopentenedione, described by (xiii), together with an ammonia source such as ammonia in ethanol, ammonium acetate, or ammonium hydroxide, may be heated in a protic solvent such as ethanol, methanol, isopropanol etc. or in dimethylformamide (DMF), or acetonitrile with an enone (xiv) component that has been prepared from an aldehyde (ii) and a carbonyl component (xv). An intermediate hemiaminal (xvi) or the desired dihydropyridine(xvii) may be isolated. In the case where the hemiaminal (xvi) is isolated, this may be converted to the dihydropyridine (xvii) by heating with an acid such as hydrochloric acid, sulfuric acid or toluenesulfonic acid under an inert atmosphere such as nitrogen or argon in order to drive the reaction to completion. This dehydration reaction may also be accomplished with $POCl_3$ in pyridine. Alternatively, 3-amino-2-cyclopenten-1-one (iv) may be substituted for 1,3-cyclopentanedione (xiii) wherein the double bond is absent, and ammonia in Path A. According to Path B, 1,3-cyclopentanedione or 1,3-cyclopentenedione (xiii) together with an ammonia source such as ammonia in ethanol, ammonium acetate, or ammonium hydroxide, may be heated in a protic solvent such as ethanol, methanol, isopropanol etc. or in dimethylformamide (DMF), or acetonitrile with a carbonyl component (xv). Any hemiaminal (xvi) intermediate obtained via this route may be converted to the dihydropyridine (xvii) as above.

According to Path B, 3-amino-2-cyclopenten-1-one (iv) may be reacted with an aldehyde (ii) and an appropriate carbonyl component (xix) using the same reaction conditions as for Path A. According to Path C, 1,3-cyclopentanedione or 1-3-cyclopentenedione (xiii) together with an ammonia source such as ammonia in ethanol, ammonium acetate, or ammonium hydroxide, may be reacted using the same conditions as for Path A with an enone component (xx) that has been prepared from an aldehyde (ii) and a carbonyl component (xix). Alternatively in Path C, 3-amino-2-cyclopenten-1-one (iv) may be substituted for the 1,3-cyclopentanedione (xiii) wherein the double bond is absent, and the ammonia source using the same reaction conditions.

Scheme 6

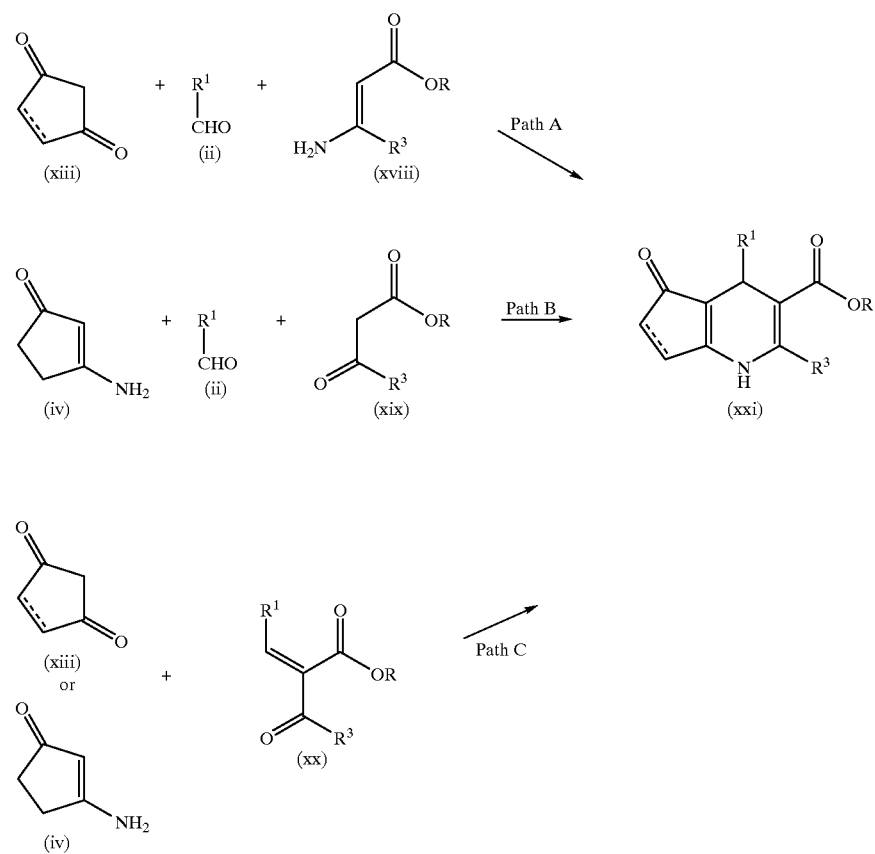

As shown in Scheme 6, the dihydropyridines of formula (xxi), wherein $R^1$ and $R^3$ are as defined in formula I and R is selected from alkyl, arylalkyl, cyanoalkyl, and a carboxy protecting group, can be prepared by one of three general methods. According to Path A, 1,3-cyclopentanedione or 1,3-cyclopentenedione (xiii) may be reacted with an aldehyde (ii) and an appropriate enamine component (xviii) with heating in a protic solvent such as ethanol, methanol, isopropanol etc. or in dimethylformamide (DMF), or acetonitrile. A subsequent period of heating may be required with an acid such as hydrochloric acid, sulfuric acid or toluenesulfonic acid in order to drive the reaction to completion.

Scheme 7

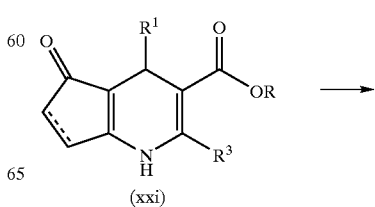

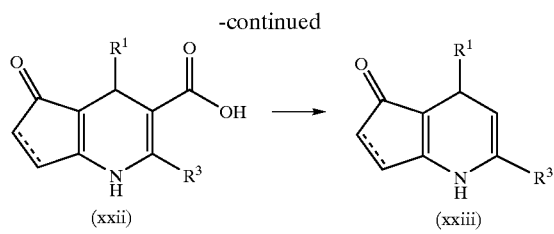

In Scheme 7, dihydropyridines (xxiii) can be prepared from the carboxylic esters (xxi), wherein $R^1$ and $R^3$ are as defined in formula I and R is selected from alkyl, arylalkyl, cyanoalkyl, and a carboxy protecting group. The esters may be cleaved to the carboxylic acids (xxii) using a variety of conditions dependent upon the nature of the group R. In cases where R is an alkyl group this process may be best accomplished with boron trichloride ($BCl_3$) in a solvent such as dichloromethane or chloroform. For cases where R is cyanoethyl, this cleavage is accomplished by treatment with base such as potassium carbonate in a solvent such as. Other types of esters may be removed by methods well-known to those skilled in the art such as acid treatment or hydrogenolysis. The carboxylic acid group of (xxii) may also be removed by decarboxylation to give dihydropyridines (xxiii). Typical conditions include heating in a solvent such as ethanol or toluene in the absence or the presence of an acid such as hydrochloric acid, sulfuric acid or toluenesulfonic acid under an inert atmosphere such as nitrogen or argon.

can be prepared by one of two general methods. According to Path A, 1,3-cyclopentanedione or 1,3-cyclopentenedione (xiii) and an aldehyde (ii) together with an ammonia source such as ammonia in ethanol, ammonium acetate, or ammonium hydroxide, may be heated in a protic solvent such as ethanol, methanol, isopropanol etc. or in dimethylformamide (DMF), or acetonitrile with a β-ketoester component (xxiv). According to Path B, 3-amino-2-cyclopenten-1-one (iv) may be substituted for the 1,3-cyclopentanedione (xiii) wherein a double bond is absent, and ammonia source of Path A. An intermediate hemiaminal (xxv) or the desired dihydropyridine (xxvi) may be isolated. In the case where the hemiaminal (xxv) is isolated, this may be converted to the dihydropyridine (xxvi) by heating with an acid such as hydrochloric acid, sulfuric acid or toluenesulfonic acid acid under an inert atmosphere such as nitrogen or argon in order to drive the reaction to completion. This dehydration reaction may also be accomplished with $POCl_3$ in pyridine. The carboxylic esters (xxvi) may be cleaved to the carboxylic acids (xxvii) using a variety of conditions dependent upon the nature of the group R. In cases where R is an alkyl group this process may be best accomplished with boron trichloride ($BCl_3$) in a solvent such as dichloromethane or chloroform. For cases where R is cyanoethyl, this cleavage is accomplished by treatment with base such as potassium carbonate in a solvent. Other types of esters may be removed by methods well-known to those skilled in the art such as acid treatment or hydrogenolysis. The carboxylic acid (xxvii) group may also be removed by decarboxylation to give dihydropyridines (xxviii). Typical conditions include heating in a solvent such as ethanol or toluene in the absence

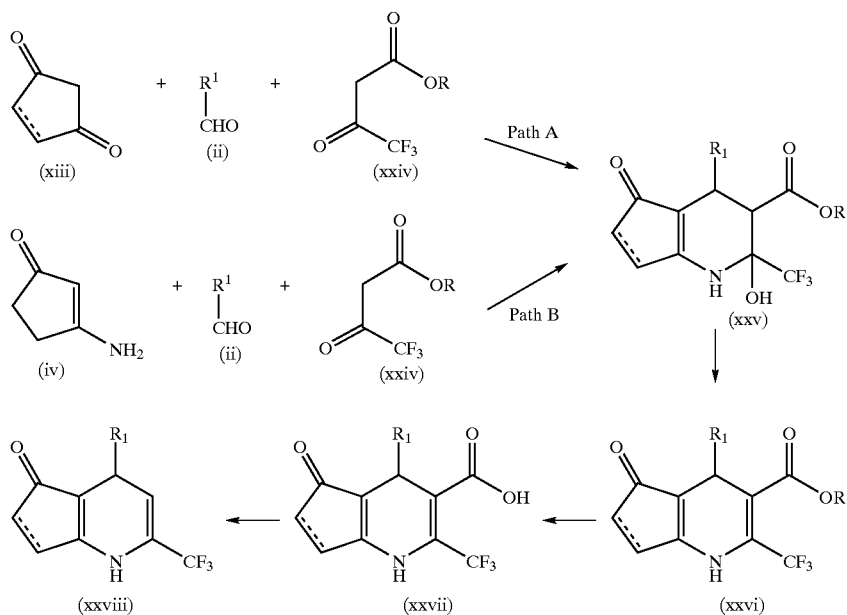

Scheme 8

As shown in Scheme 8, the hemiaminals of formula (xxv), wherein $R^1$ is defined in formula I and R is selected from alkyl, arylalkyl, cyanoalkyl, and a carboxy protecting group, or the presence of an acid such as hydrochloric acid, sulfuric acid or toluenesulfonic acid under an inert atmosphere such as nitrogen or argon.

Scheme 9

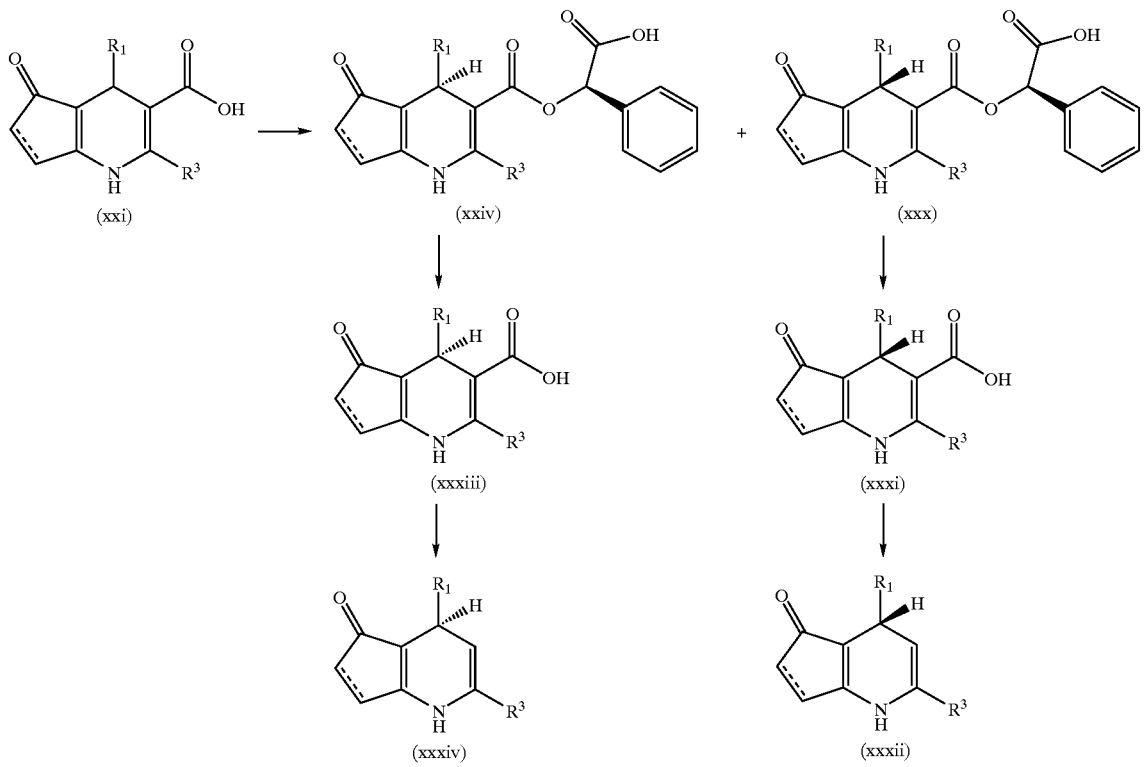

As shown in Scheme 9, wherein $R^1$ and $R^3$ are as defined in formula I, Examples of the present invention that possess a center of chirality and thus exist in racemic form may be separated into the individual enantiomers by the method shown in Scheme 9. The racemic carboxylic acid (xxi) may be converted to an intermediate acid chloride using thionylchloride, oxalylchloride or similar reagent. The acid chloride is generally not isolated but treated directly with (R) or (S) mandelic aicd to produce a mixture of diastereomeric mandelic acid esters (xxiv) and (xxx). These diastereomeric esters (xxiv) and (xxx) may be separated using column chromatography on silica gel. The individually separated mandelic acid esters (xxiv) and (xxx) may be cleaved to the enantiomerically pure carboxylic acids (xxxiii) and (xxxi) respectively, by treatment with $BCl_3$ in a solvent such as dichloromethane or chloroform. Alternatively, the mandelic acid esters (xxiv) and (xxx) may be first converted to the corresponding methyl esters by treatment with sodium methoxide in methanol prior to cleavage to the carboxylic acid as described above. Alternative methods for separating the carboxylic acids (xxiv) and (xxx) into the single enantiomers include reaction of the racemic carboxylic acid (xxi) with α-methylbenzylamine or phenylglycinol and separation of the diastereomeric salts by crystallization. The carboxylic acid group of the single enantiomers (xxxiii) and (xxxi) may also be removed by decarboxylation to give chiral dihydropyridines (xxxiv) and (xxxii) respectively. Typical conditions include heating in a solvent such as ethanol or toluene in the absence or the presence of an acid such as hydrochloric acid, sulfuric acid or toluenesulfonic acid under an inert atmosphere such as nitrogen or argon. Racemic compounds of the present invention may also be separated into the individual enantiomers by chiral chromatography.

Abbreviations

The following abbreviations are used: $K_2CO_3$ for potassium carbonate, $LiAlH_4$ for lithium aluminum hydride, $AlH_3$ for aluminum hydrate, $BH_3$ for borane, $BH_3$.DMS for borane dimethylsulfide complex, DMF for dimethylformamide, DMSO for dimethylsulfoxide, $Et_3N$ for triethylamine, $Et_2O$ for diethyl ether, EtOAc for ethyl acetate, EtOH for ethanol, KOtBu for potassium tert-butoxide, LDA for lithium diisopropylamide, MeOH for methanol, NaOMe for sodium methoxide, NaOH for sodium hydroxide, HCl for hydrochloric acid, $H_2$/Pd for hydrogen and a palladium catalyst, iPrOH for isopropyl alcohol and THF for tetrahydrofuran, cat. TFA for catalytic trifluoroacetic acid, TFA for catalytic trifluoroacetic acid, $PPh_3/CCl_4$ for triphenyl phosphine/carbon tetrachloride, and n-BuLi for n-butyllithium.

The compounds and processes of the present invention will be better understood by reference to the following examples, which are intended as an illustration of and not a limitation upon the scope of the invention. Further, all citations herein are incorporated by reference.

EXAMPLE 1

8-(3-Bromo-4-fluorophenyl)-2,3,4,5,6,8-hexahydrocyclopenta[b,e]pyridine-1,7-dione A solution of 3-aminocyclopent-2-en-1-one (97 mg, 1.0 mmol), 1,3-cyclopentanedione (98 mg, 1.0 mmol) and 3-bromo-4-fluorobenzaldehyde (203 mg, 0.99 mmol) in ethyl alcohol (4 mL) was heated to 80° C. for 3 days in a sealed tube. The reaction was cooled, solvent evaporated and the crude flash chromatographed (5% methyl alcohol/methylene chloride) to provide 133 mg of an intermediate hemiaminal. This intermediate was treated with 1.0 M HCl/diethyl ether (1 mL) in ethyl alcohol with heating to reflux overnight. The reaction was cooled, the solvent evaporated, the solid triturated with hot ethyl acetate, collected, washed with ethyl acetate and dried to provide 96 mg of the title compound as a tan solid.

$^1$H NMR (DMSO-d$_6$) δ2.32 (m, 4H), 2.55–2.80 (m, 4H), 4.51 (s, 1H), 7.21 (m, 2H), 7.44 (dd, 1H), 10.63 (s, 1H);

MS (APCI–) m/z 360 (M–H)$^-$;

Anal. calcd for C$_{17}$H$_{13}$BrFNO$_2$: C, 56.37; H, 3.61; N, 3.86. Found: C, 56.80; H, 3.89; N, 3.53.

EXAMPLE 2

8-(3-Cyanophenyl)-2,3,4,5,6,8-hexahydrodicyclopenta[b,e]pyridine-1,7-dione

3-Cyanobenzaldehyde (0.131 g, 1.00 mmol) was processed as in Example 1. Purification by flash chromatography (5% methyl alcohol/methylene chloride) provided 0.136 g of the title compound as a gray solid.

$^1$H NMR (DMSO-d$_6$) δ2.32 (t, 4H), 2.68 (m, 4H), 4.58 (s, 1H), 7.43 (t, 1H), 7.55 (m, 3H) 10.61 (s, 1H);

MS (APCI+) m/z 291 (M+H)$^+$, MS (APCI–) m/z 289 (M–H)$^-$;

Anal. calcd for C$_{18}$H$_{14}$N$_2$O$_2$•0.6 H$_2$O: C, 71.80; H, 5.09; N, 9.30. Found: C, 71.48; H, 5.22; N, 8.90.

EXAMPLE 3

8-(4-Chloro-3-nitrophenyl)-2,3,4,5,6,8-hexahydrodicyclopenta[b,e]pyridine-1,7-dione 4-Chloro-3-nitrobenzaldehyde (0.186 g, 1.00 mmol) was processed as in Example 1. The product was collected, washed with ethyl alcohol and dried to provide 0.110 g of the title compound as a gray solid.

$^1$H NMR (DMSO-d$_6$) δ2.32 (t, 4H), 2.68 (m, 4H), 4.62 (s, 1H), 7.52 (d, 1H), 7.62 (d,2H), 7.80 (s, 1H), 10.68 (s, 1H);

MS (APCI+) m/z 345 (M+H)$^+$, MS (APCI–) m/z 343 (M–H)$^-$;

Anal. calcd for C$_{17}$H$_{13}$ClN$_2$O$_4$•0.2 H$_2$O: C, 58.61; H, 3.88; N, 8.04. Found: C, 58.57; H, 4.24; N, 7.66.

EXAMPLE 4

8-(3-Nitrophenyl)-2,3,4,5,6,8-hexahydrodicyclopenta[b,e]pyridine-1,7-dione

3-Nitrobenzaldehyde (0.151 g, 1.00 mmol) was processed as in Example 1. The solid was collected, washed with ethyl alcohol and dried to provide 0.120 g of the title compound as a yellow solid.

$^1$H NMR (DMSO-d$_6$) δ2.32 (t, 4H), 2.70 (m, 4H), 4.67 (s, 1H), 7.54 (t, 1H), 7.65 (d,1H), 8.01 (m, 2H), 10.68 (s, 1H);

MS (APCI+) m/z 311 (M+H)$^+$, MS (APCI–) m/z 309 (M–H)$^-$;

Anal. calcd for C$_{17}$H$_{14}$N$_2$O$_4$: C, 65.80; H, 4.55; N, 9.03. Found: C, 65.56; H, 4.55; N, 8.95.

EXAMPLE 5

8-(3-Chloro-4-fluorophenyl)-2,3,4,5,6,8-hexahydrodicyclopenta[b,e]pyridine-1,7-dione 3-Chloro-4-fluorobenzaldehyde (0.158 g, 1.00 mmol) was processed as in Example 1. The solid was collected, washed with methylene chloride and dried to provide 0.113 g of the title compound as a pink solid.

$^1$H NMR (DMSO-d$_6$) δ2.32 (t, 4H), 2.67 (m, 4H), 4.51 (s, 1H), 7.16 (m, 1H), 7.25 (t, 1H), 7.32 (d, 1H), 10.61 (s, 1H);

MS (APCI+) m/z 318 (M+H)$^+$, MS (APCI–) m/z 316 (M–H)$^-$;

Anal. calcd for C$_{17}$H$_{13}$ClFNO$_2$•0.25 CH$_2$Cl$_2$.

EXAMPLE 6

8-(3,4-Dichlorophenyl)-2,3,4,5,6,8-hexahydrodicyclopenta[b,e]pyridine-1,7-dione 3,4-Dichlorobenzaldehyde (0.175 g, 1.00 mmol) was processed as in Example 1. The solid was collected, washed with ethyl alcohol and dried to provide 0.164 g of the title compound as a pink solid.

$^1$H NMR (DMSO-d$_6$) δ2.32 (t, 4H), 2.67 (m, 4H), 4.52 (s, 1H), 7.17 (d, 1H), 7.38 (s, 1H), 7.49 (d, 1H), 10.64 (s, 1H);

MS (APCI+) m/z 334 (M+H)$^+$; MS (APCI–) m/z 332 (M–H)$^-$;

Anal. calcd for C$_{17}$H$_{13}$Cl$_2$NO$_2$•025 CH$_2$Cl$_2$: C, 58.29; H, 3.83; N, 3.94. Found: C, 58.14; H, 4.18; N, 3.92.

EXAMPLE 7

8-(2,1,3-benzoxadiazol-5-yl)-2,3,4,5,6,8-hexahydrodicyclopenta[b,e]pyridine-1,7-dione 2,1,3-Benzoxadiazole-5-aldehyde (0.296 g, 2.00 mmol), prepared according to the method of Gasco (*Eur. J. Med. Chem.* 1996, 31, 3), was processed as in Example 1. The crude product was purified by flash chromatography over silica gel (10% ethanol/methylene chloride) to provide 0.10 g of the title compound.

mp 272–273° C.;

$^1$H NMR (DMSO-d$_6$) δ2.34 (t, 4H), 2.53–2.81 (m, 4H), 4.68 (s, 1H), 7.63 (d, 2H), 7.92 (d, 1H), 10.71 (s, 1H);

MS (ESI) m/z 308 (M+H)$^+$;

Anal. calcd for C$_{17}$H$_{13}$N$_3$O$_3$•0.75H$_2$O: C, 63.64; H, 4.55; N, 13.09. Found: C, 63.76; H, 4.36; N, 12.74.

EXAMPLE 8

8-(3-Iodo-4-fluorophenyl)-2,3,4,5,6,8-hexahydrodicyclopenta[b,e]pyridine-1,7-dione

EXAMPLE 8A

3-Amino-4-fluorobenzyl alcohol

3-Amino-4-fluorobenzoic acid (15 g, 97 mmol) in THF at 0° C. was treated with 1.0 M BH$_3$•THF (50 mL) with stirring overnight at room temperature. An additional 130 mL 1.0 M BH$_3$•THF was added with stirring for 10 hours. The reaction mixture was quenched by the addition of methanol, stirred 3 hours at room temperature, solvent evaporated, and the product partitioned between aqueous sodium bicarbonate/methylene chloride. The organic layer was dried (sodium sulfate), filtered, and the solvent evaporated. The crude product was purified by flash chromatography over silica gel (ethyl acetate/hexane 1:1) to provide 7.0 g of the title compound.

$^1$H NMR (CDCl$_3$) δ4.58 (s, 2H), 6.67 (br m, 1H), 6.81 (d, 1H), 6.95 (t, 1H).

EXAMPLE 8B

4-Fluoro-3-iodobenzylalcohol

The product from Example 8A (7.0 g, 50 mmol) in water (100 mL) at 0° C. was treated slowly with concentrated sulfuric acid (30 mL) at a rate to maintain the temperature below 10° C., then treated dropwise with an aqueous solution of sodium nitrite (3.45 g, 50 mmol). This solution was then added to a solution of potassium iodide (8.13 g, 50 mmol) in water (15 mL), heated to 60° C. for 2 hours, cooled, and extracted with methylene chloride. The organic phase was washed with 10% sodium hydroxide, 1 M sodium thiosulfate, 10% hydrochloric acid, aqueous sodium bicarbonate, dried (sodium sulfate), filtered, and the solvent evaporated. The crude product was purified by flash chromatography over silica gel (ethyl acetate/hexane 7:3) to provide 6.4 g of the title compound.

$^1$H NMR (CDCl$_3$) δ1.69 (t, 1H), 4.66 (d, 2H), 7.05 (t, 1H), 7.60 (d, 1H), 7.78 (dd, 1H).

EXAMPLE 8C

4-Fluoro-3-iodobenzaldehyde

The product from Example 8B (6.4 g, 26 mmol) in chloroform (300 mL) was treated with manganese dioxide (4.5 g, 50 mmol) and stirred overnight. Additional manganese dioxide (2.25 g) was added to the reaction mixture and stirred overnight. The slurry was filtered and the solvent evaporated. The crude product was purified by flash chromatography over silica gel (ethyl acetate/hexane 1:4) to provide 1.9 g of the title compound.

$^1$H NMR (CDCl$_3$) δ7.23 (t, 1H), 7.89 (m, 1H), 8.32 (dd, 1H), 9.91 (s, 1H).

EXAMPLE 8D 8-(3-Iodo-4-fluorophenyl)-2,3,4,5,6,8-hexahydrodicyclopenta[b,e]pyridine-1,7-dione 4-Fluoro-3-iodobenzaldehyde (0.50 g, 2.0 mmol), was processed as in Example 1 to provide 0.30 g of the title compound.

$^1$H NMR (DMSO-d$_6$) δ2.82 (t, 4H), 2.55–2.79 (m, 4H), 4.48 (s, 1H), 7.1 (t, 1H), 7.16 (m, 1H), 7.58 (dd, 1H);

MS (ESI) m/z 410 (M+H)$^+$;

Anal. calcd for C$_{17}$H$_{13}$FINO$_2$: C, 49.89; H, 3.20; N, 3.42. Found: C, 49.62; H, 3.36; N, 3.28.

EXAMPLE 9

9-(3-bromo-4-fluorophenyl)-5,6,7,9-tetrahydro-1H-cyclopenta[b]quinoline-1,8(4H)-dione A solution of 4-cyclopentene-1,3-dione (1.14 g, 10.2 mmol), 3-bromo-4-fluorobenzaldehyde (2.05 g, 10.1 mmol), and 3-amino-2-cyclohexenone (1.14 g, 10.2 mmol) in absolute ethanol (50 mL) were magnetically stirred and heated at reflux for 36 hours. The mixture was vacuum filtered and the solid was washed with ethyl acetate-hexane. The filtrate was concentrated and the residue was chromatographed on silica gel (100 g) using EtOAc-hexane (75:25), then EtOAc, finally EtOAc—EtOH (95:5). The product was obtained as a tan crystalline solid, (720 mg, 1.92 mmol).

mp>260.

$^1$H NMR (DMSO-d$_6$) δ1.79 (m, 1H); 1.90 (m, 1H), 2.20 (m, 2H), 2.54 (m, 2H), 4.86 (s, 1H), 7.15 (m, 4H), 7.38 (dd, 1H, J=6.8, 2.0 Hz), 9.52 (s, 1H);

MS (APCI+) m/z 390 (M+18)$^+$;

Anal. Calcd for C$_{18}$H$_{13}$BrFNO$_2$: C, 57.77; H, 3.50; N, 3.74. Found: C, 57.62; H, 3.56; N, 3.58.

EXAMPLE 10

4-(3-bromo-4-fluorophenyl)-2-methyl-5-oxo-4,5,6,7-tetrahydro-1H-cyclopenta[b]pyridine -3-carboxylic acid

EXAMPLE 10A methyl 4-(3-bromo-4-fluorophenyl)-2-methyl-5-oxo-4,5,6,7-tetrahydro-1H-cyclopenta[b]pyridine-3-carboxylate 3-Bromo-4-fluorobenzaldehyde (3.045 g, 15 mmol), methyl acetoacetate (2.09 g, 18 mmol) and 3-aminocyclopent-2-enone (1.45 g, 15 mmol) were heated to 65° C. in methyl alcohol for 5 days. The reaction was allowed to cool to ambient temperature and the white precipitate collected, washed with methyl alcohol and dried to provide 2.29 g of the title compound. Flash chromatography (5% methyl alcohol/methylene chloride) of the filtrate provided an additional 1.46 g of the title compound.

$^1$H NMR (300 MHz, CDCl$_3$) δ2.45 (s, 3H), 3.60 (s, 3H), 4.90 (s, 1H), 6.33 (s, 1H), 6.98 (t, 1H), 7.23 (m, 1H), 7.37 (d, 1H);

MS (APCI+) m/z 380 (M+H)$^+$;

Anal. calcd for C$_{17}$H$_{15}$BrFNO$_3$: C, 53.70; H, 3.98; N, 3.68. Found: C, 53.57; H, 3.91; N, 3.48.

EXAMPLE 10B 4-(3-bromo-4-fluorophenyl)-2-methyl-5-oxo-4,5,6,7-tetrahydro-1H-cyclopenta[b]pyridine-3-carboxylic acid A suspension of the product from Example 10A (1.90 g, 5.0 mmol) in methylene chloride (10 mL) at 5° C. under nitrogen was treated with 1M boron trichloride in methylene chloride (40 mL), stirred overnight, quenched in ice water (100 mL) and ethyl acetate (30 mL), and the aqueous drained off. The suspension of the product in ethyl acetate was filtered, the filter cake was washed with ethyl acetate and dried to provide 1.26 g of the title compound as an orange-pink solid.

mp 211–214° C.;

$^1$H NMR (DMSO-d$_6$) δ2.24 (t, 2H), 2.33 (s, 3H), 2.55 (t, 2H), 4.68 (s, 1H), 7.17 (m, 1H), 7.23 (t, 1H), 7.38 (d, 1H), 9.72 (s, 1H), 11.87 (s, 1H);

MS (APCI−) m/z 364 (M−H)$^-$;

Anal. Calcd for C$_{16}$H$_{13}$BrFNO$_3$ 0.25 H$_2$O: C, 51.84; H, 3.67; N, 3.78. Found: C, 51.62; H, 3.90; N, 3.62.

Determination of Potassium Channel Opening Activity Membrane Hyperpolarization Assays Compounds were evaluated for potassium channel opening activity using primary cultured guinea-pig urinary bladder (GPB) cells.

For the preparation of urinary bladder smooth muscle cells, urinary bladders were removed from male guinea-pigs (Hartley, Charles River, Wilmington, Mass.) weighing 300–400 g and placed in ice-cold Ca$^{2+}$-free Krebs solution (Composition, mM: KCl, 2.7; KH$_2$PO$_4$, 1.5; NaCl, 75; Na$_2$HPO$_4$, 9.6; Na$_2$HPO$_4$·7H$_2$O, 8; MgSO$_4$, 2; glucose, 5; HEPES, 10; pH 7.4). Cells were isolated by enzymatic dissociation as previously described with minor modifications (Klockner, U. and Isenberg, G., *Pflugers Arch.* (1985), 405, 329–339), hereby incorporated by reference. The bladder was cut into small sections and incubated in 5 mL of the Kreb's solution containing 1 mg/mL collagenase (Sigma, St. Louis, Mo.) and 0.2 mg/mL pronase (Calbiochem, La Jolla, Calif.) with continuous stirring in a cell incubator for 30 minutes. The mixture was then centrifuged at 1300×g for 5 minutes, and the pellet resuspended in Dulbecco's PBS (GIBCO, Gaithersburg, Md.) and recentrifuged to remove residual enzyme. The cell pellet was resuspended in 5 mL growth media (composition: Dulbecco's modified Eagle's medium supplemented with 10% fetal bovine serum, 100 units/mL penicillin, 100 units/mL streptomycin and 0.25 mg/mL amphotericin B) and further dissociated by pipetting the suspension through a flame-polished Pasteur pipette and passing it through a polypropylene mesh membrane (Spectrum, Houston, Tex.). The cell density was adjusted to 100,000 cells/mL by resuspension in growth media. Cells were plated in clear-bottomed black 96-well plates (Packard) for membrane potential studies at a density of 20,000 cells/well and maintained in a cell incubator with 90% air: 10% $CO_2$ until confluent. Cells were confirmed to be of smooth muscle type by cytoskeletal staining using a monoclonal mouse anti human-α-smooth muscle actin (Biomeda, Foster City, Calif.)

Functional activity at potassium channels was measured by evaluating changes in membrane potential using the bis-oxonol dye DiBAC(4)$_3$ (Molecular Probes) in a 96-well cell-based kinetic assay system, Fluorescent Imaging Plate Reader (FLIPR) (K. S. Schroeder et al., *J. Biomed. Screen.*, v. 1 pp. 75–81 (1996)), hereby incorporated by reference. DiBAC(4)$_3$ is an anionic potentiometric probe which partitions between cells and extracellular solution in a membrane potential-dependent manner. With increasing membrane potential (for example, $K^+$ depolarization), the probe further partitions into the cell; this is measured as an increase in fluorescence due to dye interaction with intracellular lipids and proteins. Conversely, decreasing membrane potential (hyperpolarization by potassium channel openers) evokes a decrease in fluorescence.

Confluent guinea-pig urinary bladder cells cultured in black clear-bottomed 96-well plates were rinsed twice with 200 mL assay buffer (composition, mM: HEPES, 20; NaCl, 120; KCl, 2; CaCl$_2$, 2; MgCl$_2$, 1; glucose, 5; pH 7.4 at 25° C.) containing 5 μM DiBAC(4)$_3$ and incubated with 180 mL of the buffer in a cell incubator for 30 minutes at 37° C. to ensure dye distribution across the membrane. After recording the baseline fluorescence for 5 minutes, the reference or test compounds, prepared at 10 times the concentration in the assay buffer, were added directly to the wells. Changes in fluorescence were monitored for an additional 25 minutes. Hyperpolarization responses were corrected for any background noise and were normalized to the response observed with 10 μM of the reference compound P1075 (assigned as 100%), a potent opener of smooth muscle $K_{ATP}$ channels (Quast et al., *Mol. Pharmacol.*, v. 43 pp. 474–481 (1993)), hereby incorporated by reference.

Routinely, five concentrations of P1075 or test compounds (log or half-log dilutions) were evaluated and the maximal steady-state hyperpolarization values (expressed as % relative to P1075) plotted as a function of concentration. The $EC_{50}$ (concentration that elicites 50% of the maximal response for the test sample) values were calculated by non-linear regression analysis using a four parameter sigmoidal equation. The maximal response of each compound (expressed as % relative to P1075) is reported. Stock solutions of compounds were prepared in 100% DMSO and further dilutions were carried out in the assay buffer and added to a 96-well plate.

TABLE 1

Membrane Hyperpolarization (MHP) in Guinea-Pig Bladder (GPB) Cells

| Example # | Maximal Response (% P1075) | $EC_{50}$ (μM) |
| --- | --- | --- |
| 1 | 102 | 0.071 |
| 2 | 65 | 5.3 |
| 3 | 113 | 0.053 |
| 4 | 123 | 0.34 |
| 5 | 72 | 0.14 |
| 6 | 94 | 0.10 |
| 7 | 98 | 0.13 |
| 8 | 93 | 0.013 |
| 9 | 100 | 0.063 |
| 10 | 103.5 | 2.68 |

In vitro Functional Models

Compounds were evaluated for functional potassium channel opening activity using tissue strips obtained from Landrace pig bladders.

Landrace pig bladders were obtained from female Landrace pigs of 9–30 kg. Landrace pigs were euthanized with an intraperitoneal injection of pentobarbital solution, Somlethal®, J. A. Webster Inc., Sterling Mass. The entire bladder was removed and immediately placed into Krebs Ringer bicarbonate solution (composition, mM: NaCl, 120; NaHCO$_3$, 20; dextrose, 11; KCl, 4.7; CaCl$_2$, 2.5; MgSO$_4$, 1.5; KH$_2$PO$_4$, 1.2; K$_2$EDTA, 0.01, equilibrated with 5% CO$_2$/95% O$_2$ pH 7.4 at 37° C.). Propranolol (0.004 mM) was included in all of the assays to block β-adrenoceptors. The trigonal and dome portions were discarded. Strips 3–5 mm wide and 20 mm long were prepared from the remaining tissue cut in a circular fashion. The mucosal layer was removed. One end was fixed to a stationary glass rod and the other to a Grass FT03 transducer at a basal preload of 1.0 gram. Two parallel platinum electrodes were included in the stationary glass rod to provide field stimulation of 0.05 Hz, 0.5 milli-seconds at 20 volts. This low frequency stimulation produced a stable twitch response of 100–500 centigrams. Tissues were allowed to equilibrate for at least 60 minutes and primed with 80 mM KCl. A control concentration response curve (cumulative) was generated for each tissue using the potassium channel opener P1075 as the control agonist. P1075 completely eliminated the stimulated twitch in a dose dependent fashion over a concentration range of $10^{-9}$ to $10^{-5}$ M dissolved in DMSO using ½ log increments. After a 60 minute rinsing period, a concentration response curve (cumulative) was generated for the test agonist in the same fashion as that used for the control agonist P1075. The maximal efficacy of each compounds (expressed as % relative to P1075) is reported. The amount of agent necessary to cause 50% of the agent's maximal response ($ED_{50}$) was calculated using "ALLFIT" (DeLean et al., *Am. J. Physiol.* 235, E97 (1980)), hereby incorporated by reference, and agonist potencies were expressed as pD$_2$ (the negative logarithm). Agonist potencies were also expressed as an index relative to P1075. The index was calculated by dividing the $ED_{50}$ for P1075 by the $ED_{50}$ for the test agonist in a given tissue. Each tissue was used for only one test agonist, and the indices obtained from each tissue were averaged to provide an average index of potency. These data are shown in Table 2.

TABLE 2

Functional Potassium Channel Opening Activity in Isolated Bladder Strips

Landrace Pig Bladder

| Example # | Efficacy (% P1075) | pD2 | Index |
|---|---|---|---|
| 1 | 98 | 6.8 | 0.48 |
| 2 | 96 | 5.2 | 0.017 |
| 3 | 98 | 6.6 | 0.35 |

As shown by the data in Tables 1 and 2, the compounds of this invention reduce stimulated contractions of the baldder.

In Vivo Data

The utility of compounds of the present invention for the treatment of urinary incontinence may be illustrated by the ability of compounds of the invention to inhibit bladder contractions in-vivo. The following method may be illustrative of the in-vivo bladder efficacy of compounds of the invention. Importantly, several compounds known from publications lack sufficient solubility in the dosing vehicle used for intravenous administration.

In-vivo bladder efficacy protocol (isovolumetric contractions model)

Male CD rats (400–450 g) were anesthetized with urethane (0.6 g/kg ip+0.6 g/kg sc). The left femoral artery and vein were cannulated with polyethylene (PE-50) tubing for the measurement of arterial pressure and test compound administration respectively. A third polyethylene catheter (PE-60) was inserted 3–4 mm into the apex of the bladder dome and secured using a 5-0 silk purse string suture. The bladder was emptied via this catheter and additionally by applying slight manual pressure on the lower abdomen. The urinary catheter was connected using a Y-tube connector to both a pressure transducer and a syringe pump. The urethra was then ligated using 4-0 silk suture and the bladder was slowly filled using a constant infusion of room temperature saline at the rate of 0.1 ml/min until spontaneous rhythmic contractions were evident (1.0–1.3 ml). After the contractions stabilized to a consistent pattern, bladder pressure and arterial pressure were monitored for 20 minutes before and after a dose of the vehicle (equal parts of β-cyclodextrin stock solution (100 g β-cyclodextrin dissolved in 200 ml) and sterile water) alone. Then three doses of a test compound were administered cumulatively intravenous (iv) at 20 minute intervals. Each dosing solution (1 ml/kg) was warmed to body temperature before dosing and was infused over 3 minutes to minimize dosing artifacts on the bladder pressure trace. Data were averaged over the last 10 minutes of each period and presented as percent change from control. Mean arterial pressure and area under the curve of the bladder contractions were determined from the respective waveforms using a Modular Instruments, Inc. computerized data acquisition system and averaged over the last ten minutes of each twenty minute period. The doses required to reduce the mean arterial pressure by 15% (MAP ED15%) and reduce the area under the curve of the bladder contractions by 30% (AUC ED30%) relative to control were estimated using a customized Excel spreadsheet.

Example 3, of the present invention (Table 3, FIG. 1), was dosed at 0.01, 0.1 and 1 μmol/kg. The AUC $ED_{30}$ for Example 3 was determined to be 0.1 μmol/kg. As a comparison, Example A (Table 3, FIG. 1), the analogous compound of Example 3, was insufficiently soluble in the dosing vehicle to construct the same dose-response relationship and calculation of an AUC $ED_{30}$.

TABLE 3

Inhibition of Bladder Contractions In-Vivo

FIG. 1

| Example | R (FIG. 1) | n (FIG. 1) | AUC $ED_{30}$ (μmol/kg) |
|---|---|---|---|
| 3 | 3-$NO_2$, 4-Cl | 1 | 0.1 |
| A | 3-$NO_2$, 4-Cl | 2 | * |

(*denotes inability to procure data due to insolubility of compound in assay media)

The data in Table 3 illustrates the ability of compounds of the present invention to inhibit bladder contractions in-vivo in the dosing vehicle used for intravenous administration.

Demonstration of Aqueous Solubility Properties of Compounds of The Invention

Aqueous solubilities were determined by shaking 60 hours at room temperature in 50 mM $NaH_2PO_4$ buffers at pH's 6.5 and 7.4. Assays were performed using reverse-phase HPLC. The solubilities are expressed in nanomoles per milliliter in Table 4.

TABLE 4

Aqueous Solubility

| Example | R (FIG. 1) | n (FIG. 1) | pH 7.4 (nmol/mL) | pH 6.5 (nmol/mL) |
|---|---|---|---|---|
| 3 | 3-$NO_2$, 4-Cl | 1 | 129 | 129 |
| A | 3-$NO_2$, 4-Cl | 2 | 2.4 | 2.4 |
| 1 | 3-Br, 4-F | 1 | 227 | 205 |
| B | 3-Br, 4-F | 2 | 3.6 | 5.1 |
| 2 | 3-CN | 1 | 1290 | 1300 |
| C | 3-CN | 2 | 24.5 | 25.8 |
| 4 | 3-$NO_2$ | 1 | 164 | 158 |
| D | 3-$NO_2$ | 2 | 2.4 | 2.7 |

The data in table 4 illustrate that representative compounds of the present invention possessing two five-membered carbocyclic rings fused to the dihydropyridine nucleus, Examples 1–4 (Table 4, FIG. 1), show vastly superior water solubility to the analogous compounds having two six-membered rings fused to the dihydropyridine nucleus, Examples A–D (Table 4, FIG. 1).

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in *IUPAC 1974 Recommendations for Section E, Fundamental Stereochemistry, Pure Appl. Chem.*, 1976, 45: 13–30. In particular, the stereochemistry at the 8-position and the point of attachment of $R^1$, as shown in formulae I and II, may independently be either (R) or (S), unless specifically noted otherwise. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formulae I–II prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrastemal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar—agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar–agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate;) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., *Methods in Cell Biology*, Volume XIV, Academic Press, New York, N. Y., (1976), p 33 et seq.

The term "pharmaceutically acceptable cation," as used herein, refers to a positively-charged inorganic or organic ion that is generally considered suitable for human consumption. Examples of pharmaceutically acceptable cations are hydrogen, alkali metal (lithium, sodium and potassium), magnesium, calcium, ferrous, ferric, ammonium, alkylammonium, dialkylammonium, trialkylammonium, tetraalkylammonium, diethanolammmonium, and choline. Cations may be interchanged by methods known in the art, such as ion exchange.

The terms "pharmaceutically acceptable salts, esters and amides," as used herein, refer to carboxylate salts, amino acid addition salts, zwitterions, esters and amides of compounds of formula I which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt," as used herein, refers to salts that are well known in the art. For example, S. M Berge et al. describe pharmaceutically acceptable salts in detail in *J. Pharmaceutical Sciences*, 66:1–19 (1977). Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, and the like, metal salts such as sodium, potassium, magnesium or calcium salts or amino salts such as ammonium, triethylamine salts, and the like, all of which may be prepared according to conventional methods.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I may be prepared according to conventional methods. It is intended that amides of the present invention include amino acid and peptide derivatives of the compounds of formula I, as well.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to the parent compound of the above formula, for example, by hydrolysis in blood. A thorough discussion is provided in T. Higuchi and V. Stella, *Pro-drugs as Novel Delivery Systems*, V. 14 of the A.C.S. Symposium Series, and in Edward B. Roche, ed., *Bioreversible Carriers in Drug Design*, American Pharmaceutical Association and Pergamon Press (1987), hereby incorporated by reference.

The term "prodrug ester group," as used herein refers, to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art. Other examples of prodrug ester groups can be found in the book "Pro-drugs as Novel Delivery Systems," by Higuchi and Stella, cited above.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active metabolites formed by in vivo biotransformation of compounds of formulae I–VI. The term pharmaceutically active metabolite, as used herein, refers to a compound formed by the in vivo biotransformation of compounds of formulae I–VI. The present invention contemplates compounds of formulae I–VI and metabolites thereof. A thorough discussion of biotransformation is provided in Goodman and Gilman's, *The Pharmacological Basis of Therapeutics*, seventh edition, hereby incorporated by reference.

The compounds of the invention, including but not limited to those specified in the examples, possess potassium channel opening activity in mammals (especially humans). As potassium channel openers, the compounds of the present invention are useful for the treatment and prevention of diseases such as asthma, epilepsy, hypertension, Raynaud's syndrome, impotence, migraine, pain, eating disorders, urinary incontinence, functional bowel disorders, neurodegeneration and stroke.

The ability of the compounds of the invention to treat asthma, epilepsy, hypertension, Raynaud's syndrome, impotence, migraine, pain, eating disorders, urinary incontinence, functional bowel disorders, neurodegeneration and stroke can be demonstrated according to the methods described (D. E. Nurse et al., *Br. J. Urol.*, v. 68 pp. 27–31 (1991); B. B. Howe et al., *J. Pharmacol. Exp. Ther.*, v. 274 pp. 884–890 (1995); K. Lawson, *Pharmacol. Ther.*, v. 70 pp. 39–63 (1996); D. R. Gehlert, et al., *Neuro-Psychopharmacol & Biol. Psychiat.*, v. 18 pp. 1093–1102 (1994); M. Gopalakrishnan et al., *Drug Development Research*, v. 28 pp. 95–127 (1993); J. E. Freedman et al., *The Neuroscientist*, v. 2 pp. 145–152 (1996); D. Spanswick et al., *Nature*, v. 390 pp. 521–25 (Dec. 4, 1997)).

Aqueous liquid compositions of the present invention are particularly useful for the treatment and prevention of asthma, epilepsy, hypertension, Raynaud's syndrome, impotence, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral administration, more preferable doses can be in the range of from about 0.01 to about 5 mg/kg/day. If desired, the effective daily dose can be divided into multiple doses for purposes of administration; consequently, single dose compositions may contain such amounts or submultiples thereof to make up the daily dose.

We claim:

1. A compound having formula I:

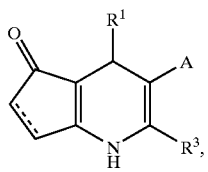

or a pharmaceutically acceptable salt thereof wherein, a broken line represents the presence of an optional double bond;

$R^1$ is phenyl or naphthyl, wherein the phenuyl or naphthyl ring can be substituted with 0, 1, 2, or 3 substituents selected from the group consisting of cyano, halogen, nitro, $C_1$–$C_6$-alkyl, halo-$C_1$–$C_6$-alkyl, and halo-$C_1$–$C_6$-alkoxy; and A and $R^3$ taken together with the ring to which they are attached can form a 5-membered carbocyclic ring, said 5-membered carbocyclic ring can contain 1 or 2 double bonds and can be substituted with 1 or 2 substituents selected from the group consisting of hydrogen, $C_2$–$C_{10}$-alkenyl, $C_1$–$C_{10}$-alkoxy, $C_1$–$C_{10}$-alkoxy-$C_1$–$C_{10}$-alkoxy, $C_1$–$C_{10}$-alkoxy-$C_1$–$C_{10}$-alkyl, $C_1$–$C_{10}$-alkyl, $C_2$–$C_{10}$-alkynyl, $C_6$–$C_{10}$-aryl-$C_1$–$C_{10}$-alkoxy, $C_2$–$C_{10}$-haloalkenyl, $C_1$–$C_{10}$-haloalkyl, halogen, hydroxy, $C_2$–$C_{10}$-hydroxyalkenyl, $C_1$–$C_{10}$-hydroxyalkyl, oxo, and —$NR^4R^5$, wherein $R^4$ and $R^5$ are independently selected from the group consisting of hydrogen and lower alkyl and wherein the aryl group in $C_6$–$C_{10}$-aryl-$C_1$–$C_{10}$-alkoxy is a carbocyclic aromatic ring.

2. A compound according to claim 1 having formula II:

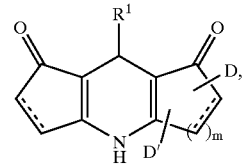

or a pharmaceutically acceptable salt thereof wherein, m is 1; and

D and D' are independently selected from the group consisting of hydrogen, $C_2$–$C_{10}$-alkenyl, $C_1$–$C_{10}$-alkoxy, $C_1$–$C_{10}$-alkoxy-$C_1$–$C_{10}$-alkoxy, $C_1$–$C_{10}$-alkoxy-$C_1$–$C_{10}$-alkyl, $C_1$–$C_{10}$-alkyl, $C_2$–$C_{10}$-alkynyl, $C_6$–$C_{10}$-aryl-$C_1$–$C_{10}$-alkoxy, $C_2$–$C_{10}$-haloalkenyl, $C_1$–$C_{10}$-haloalkyl, halogen, hydroxy, $C_2$–$C_{10}$-hydroxyalkenyl, $C_1$–$C_{10}$-hydroxyalkyl, oxo, and —$NR^4R^5$, wherein $R^4$ and $R^5$ are independently selected from the group consisting of hydrogen and lower alkyl and wherein the aryl group in $C_6$–$C_{10}$-aryl-$C_1$–$C_{10}$-alkoxy is a carbocyclic aromatic ring.

3. A compound according to claim 2 having formula III:

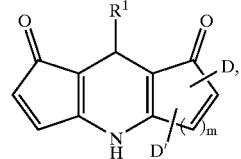

or a pharmaceutically acceptable salt thereof.

4. A compound according to claim 2 having formula IV:

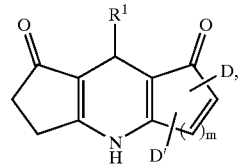

or a pharmaceutically acceptable salt thereof.

5. A compound according to claim 2 having formula V:

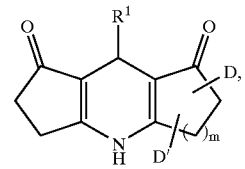

or a pharmaceutically acceptable salt thereof.

6. A compound according to claim 5 wherein, $R^1$ is phenyl or naphthyl, wherein the phenyl or naphthyl ring can be substituted with 0, 1, 2, or 3 substituents selected from the group consisting of cyano, halogen, nitro, $C_1$–$C_6$-alkyl, halo-$C_1$–$C_6$-alkyl, and halo-$C_1$–$C_6$-alkoxy;

m is 1;

D is hydrogen; and

D' is hydrogen.

7. A compound according to claim 5 wherein, $R^1$ is phenyl;

m is 1;

D is hydrogen; and

D' is hydrogen.

8. A compound according to claim 7 selected from the group consisting of 8-(3-Bromo-4-fluorophenyl)-2,3,4,5,6,8-hexahydrodicyclopenta[b,e]pyridine-1,7-dione, 8-(3-Cyanophenyl)-2,3,4,5,6,8-hexahydrodicyclopenta[b,e]pyridine-1,7-dione, 8-(4-Chloro-3-nitrophenyl)-2,3,4,5,6,8-hexahydrodicyclopenta[b,e]pyridine-1,7-dione, 8-(3-Nitrophenyl)-2,3,4,5,6,8-hexahydrodicyclopenta[b,e]pyridine-1,7-dione, 8-(3-Chloro-4-fluorophenyl)-2,3,4,5,6,8-hexahydrodicyclopenta[b,e]pyridine-1,7-dione, 8-(3,4-Dichlorophenyl)-2,3,4,5,6,8-hexahydrodicyclopenta[b,e]pyridine-1,7-dione, and 8-(3-Iodo-4-fluorophenyl)-2,3,4,5,6,8-hexahydrodicyclopenta[b,e]pyridine-1,7-dione.

9. A pharmaceutical composition comprising a therapeutically effective amount of a compound of claim 1 in combination with a pharmaceutically acceptable carrier.

10. A pharmaceutical composition comprising a therapeutically effective amount of a compound of claim 2 in combination with a pharmaceutically acceptable carrier.

* * * * *